United States Patent [19]

Völlm

[11] Patent Number: 4,827,781
[45] Date of Patent: May 9, 1989

[54] METHOD AND APPARATUS FOR THE END ALIGNMENT OF FIBERS FOR FIBER LENGTH MEASUREMENT

[75] Inventor: Ernst Völlm, Horgen, Switzerland

[73] Assignee: Siegfried Payer, AG, Wollerau, Switzerland

[21] Appl. No.: 51,534

[22] Filed: May 18, 1987

[30] Foreign Application Priority Data

May 20, 1986 [CH] Switzerland ............... 2029/86-4

[51] Int. Cl.[4] .................................................. G01N 1/04
[52] U.S. Cl. ................................................... 73/864.41
[58] Field of Search ........... 73/863.91, 863.92, 863.01, 73/863.02, 864, 864.31, 864.41, 864.42; 198/339.1; 83/919

[56] References Cited

U.S. PATENT DOCUMENTS 4,391,153  7/1983  Taylor ........................... 73/864.41
4,577,516  3/1986  Wyser ........................... 73/864.41

FOREIGN PATENT DOCUMENTS 2449630  10/1980  France ........................... 83/919

Primary Examiner—Stewart J. Levy
Assistant Examiner—Robert R. Raevis
Attorney, Agent, or Firm—Helfgott & Karas

[57] ABSTRACT

A method and apparatus for extracting a fiber sample from a sliver of material for fiber length measurement in which the sliver is successively advanced into and retained by needles in a sample extracting position with the fiber end of the sliver exposed for sampling. The end is then grasped by a clamping member which moves away from the retained sliver to extract the sample. The retention of the sliver is synchronized to follow the advancement of the sliver to its sample extracting position and the movement of the clamping member is synchronized to occur during the retention of the sliver by the needles in this sample extraction position.

6 Claims, 5 Drawing Sheets

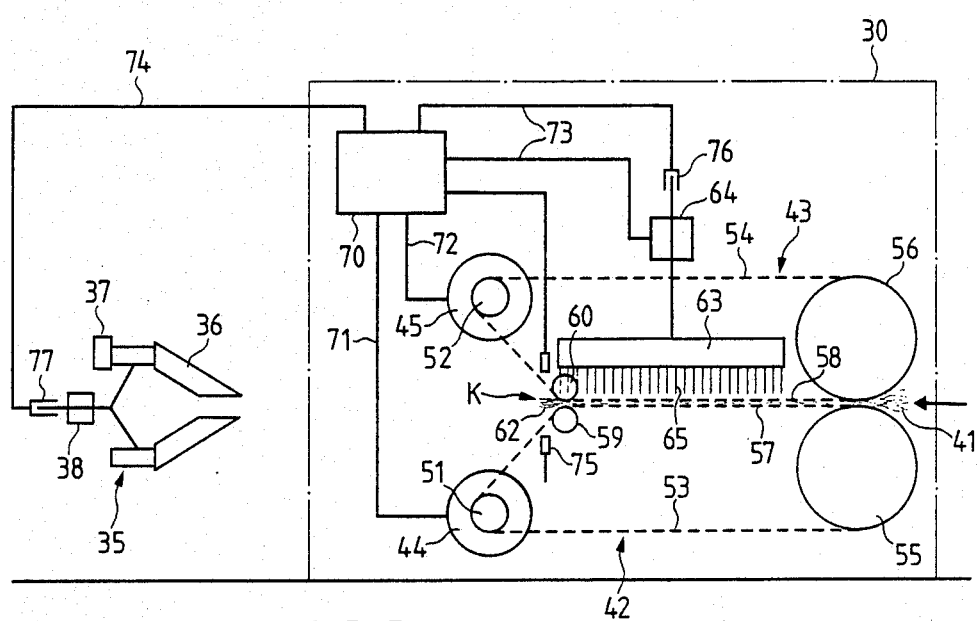
FIG. 5
FIG. 6
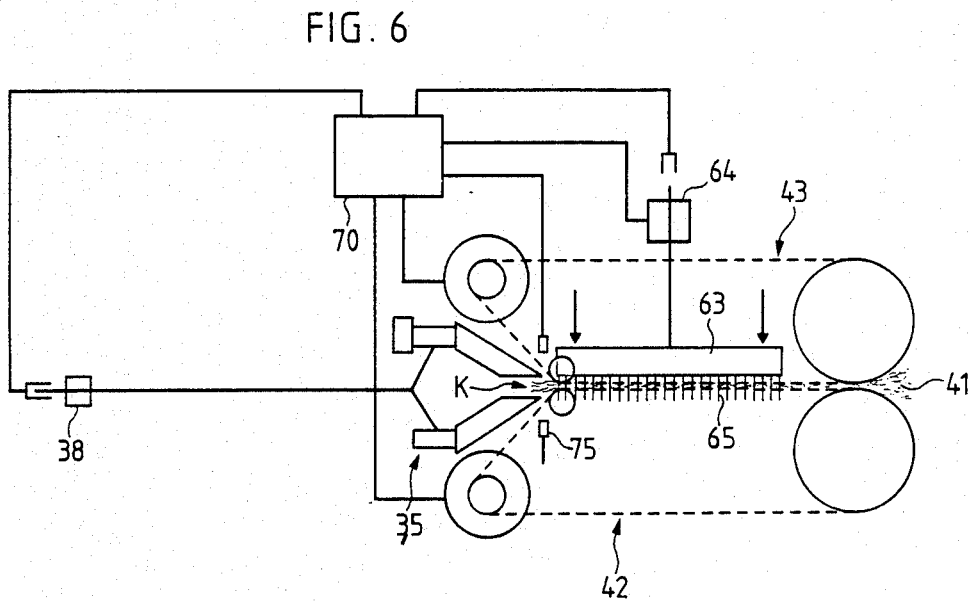

METHOD AND APPARATUS FOR THE END ALIGNMENT OF FIBERS FOR FIBER LENGTH MEASUREMENT

BACKGROUND OF THE INVENTION

The present invention relates to a method and apparatus for the alignment and extraction of a sample of the fibers of a fabric or other material for fiber length measurement, and more particularly for the extraction of a fiber sample from a sliver of material having parallelized fibers by the removal of a sample of the fiber ends of the sliver while the sliver is in a stretched position.

In order to inspect fibers having a finite length, a length measurement of the fiber is carried out whereby a representative value for the complete fiber mass is obtained. This is called a staple measurement. In obtaining such a staple measurement, particular care must be taken when extracting the sample.

In carrying out such staple measurment on textile fibers, the fiber is first prepared by forming a parallelized sliver from the material to be tested and the fiber sample is extracted from the end of the sliver maintained in end aligned manner. The fiber length in the sample is then measured, for example, capacitatively or optically, to determine the stable diagram, which is a representation of the population of the fibers arranged in accord with fiber length. The information content obtained from a fiber sample with unaligned ends is much smaller than that obtained from an end aligned sample.

The objects of the invention are to provide a method and apparatus for properly aligning the fiber ends during extraction of the sample and also to provide a fiber sample extraction method and apparatus that has greater precision, better reproducibility, reduced susceptibility to dirtying, better guidance of the fibers and better operational reliability as compared with previously known methods and apparatus.

SUMMARY OF THE INVENTION

In accord with the method of the invention, a sliver of material is successively advanced into a sample extracting position with the end of the sliver aligned and exposed for sample extraction. Needles are moved into the sliver while the sliver is in this sample extracting position to restrain the sliver against displacement. A clamping means is brought up to the exposed end of the sliver and caused to grasp the sliver end and to move away from the sliver while the sliver is restained by the needles thereby to extract the fiber sample. The needles are then moved out of the sliver and the sliver is advanced to enable the operation to be repeated.

In the apparatus for performing this method, drive means are provided for advancing the sliver into its sample extracting position, for moving the needles into and out of the sliver, for moving the clamping means toward and away from the exposed end of the sliver and for grasping the end of the sliver. Control means are also provided for synchronizing the movement of the sliver advancing means, the needles and the clamping means. The method of the invention and its control technology is thus relatively simple, and the apparatus for performing the method can be kept small and relatively inexpensive to build.

DESCRIPTION OF THE INVENTION

An embodiment of the invention and the method of practicing the invention will be described in connection with the accompanying drawings in which FIGS. 1 to 4 are diagrammatic side view representations of a fiber aligning and sample extraction apparatus in accord with the prior art while FIGS. 5 to 11 are similar diagramatic representations of the apparatus and method in accord with the invention claimed herein. More specifically:

FIG. 5 shows the fiber aligning and sample extration apparatus of the invention in its waiting position.

FIG. 6 shows the penetration of the needles of the invention into the sliver and the movement of the clamping means into its sample extraction position.

Figure 1:
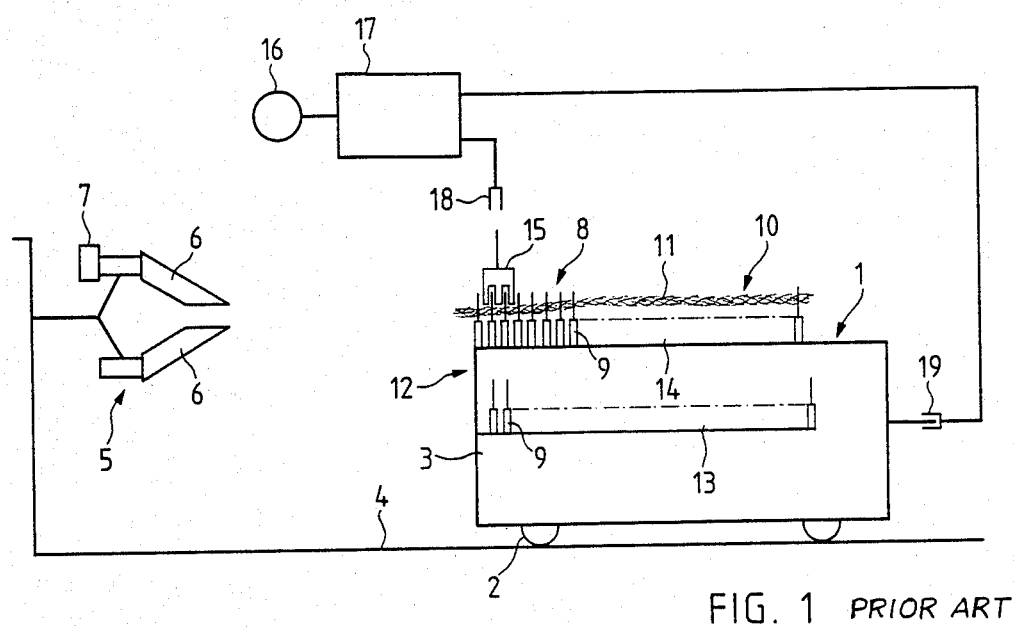
FIG. 1 shows the prior art apparatus in its waiting position.

Referring to FIGS. 1 to 4, the prior art fiber aligning and sample extracting apparatus has a trolley or truck 1 comprising a chassis 2 and a casing 3, which can be moved backwards and forwards on a base 4. A clamping member 5, which may be a gripper, is also supported on base 4. Clamping member 5 has two jaws 6 with at least one jaw operated by a drive 7, which may be a lever mechanism, for opening and closing the clamping member 5.

Truck 1 carries a needle field 8 which comprises a plurality of individual needles arranged in rows on needle combs 9. A material sample 10 is manually inserted on and into the needle field 8. Material sample 10 is appropriately in the form of a sliver 11 of fabric or other material.

Needle combs 9 are part of a conveyor system 12 in which, following each extraction of a fiber sample, the furthest forward needle comb 9 is conveyed into the lower side or strand 13, so that new fiber ends of the sliver are available for grasping by clamping member 5. The needle combs 9 in the lower side 13 are conveyed to the rear end of the upper side or strand 14 and supplement the needle field 8, which, following the extraction of the fiber sample, has delivered the furthest forward comb 9 conveyed in the lower side 13.

In order that the extraction process always takes place under the same conditions, a pressing device 15 is positioned above the needle field and is essentially constituted by a rack with a number webs, whose spacing corresponds to that of the needle combs 9 in needle field 8. The pressing-device 15 presses the sliver 11 into needle field 8. During the extraction of the fiber sample, pressing-in device 15 remains in its lowered position and keeps the sliver in position. A central drive 16 with a control system 17 is provided for operation of the truck 1 and pressing device 15.

An indicator 18 for indicating the position of pressing-device 15 and an indicator 19 for indicating the position of truck 1 are also provided.

The operation of the prior art fiber aligning apparatus will be described with reference to FIGS. 2 to 4, using the same reference numerals as in FIG. 1.

Figure 2:
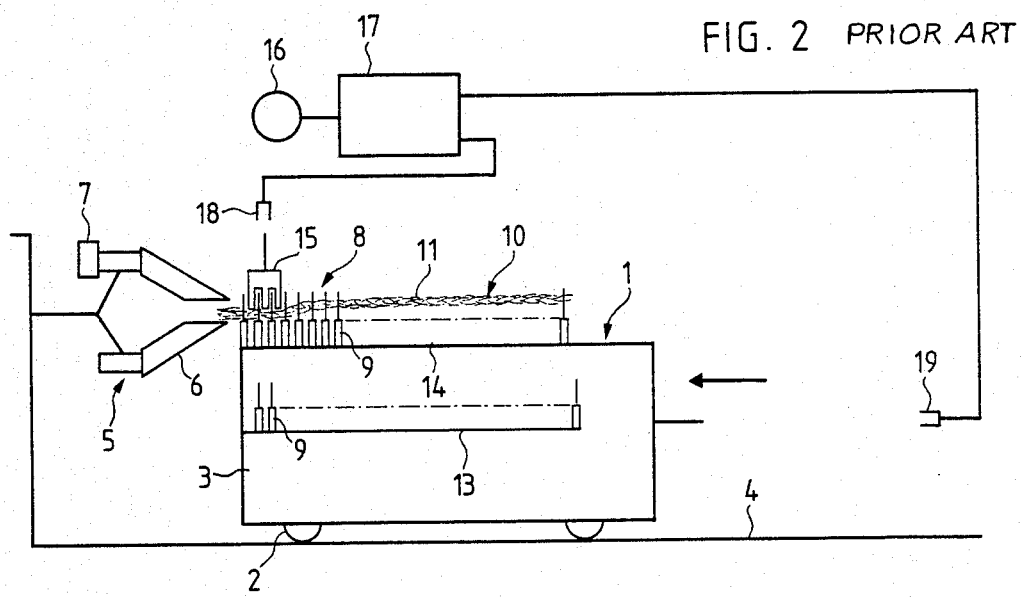
FIG. 2 shows the movement of the prior art apparatus into its sample extracting position.

In FIG. 2, truck 1 is advanced against clamping member 4, so that jaws 6 can clamp the fiber ends of fabric 11.

Figure 3:
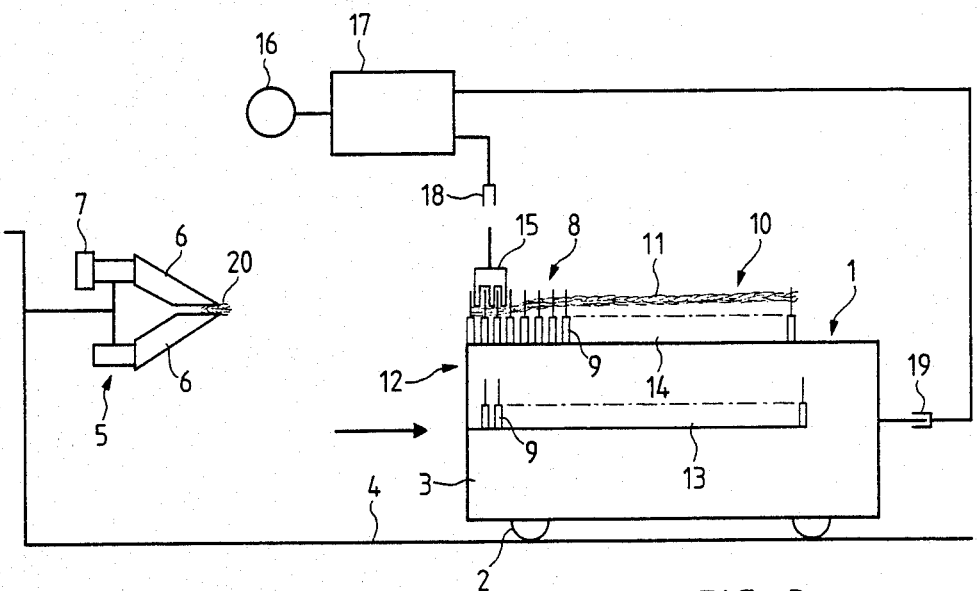
FIG. 3 shows the extraction of the fiber sample from a secured sliver and the return of the prior art apparatus to its waiting position.

In FIG. 3, the extraction process is ended. Truck 1 has once again been moved into the waiting position, while the clamping member 5 retains a fiber sample 20.

Figure 4:
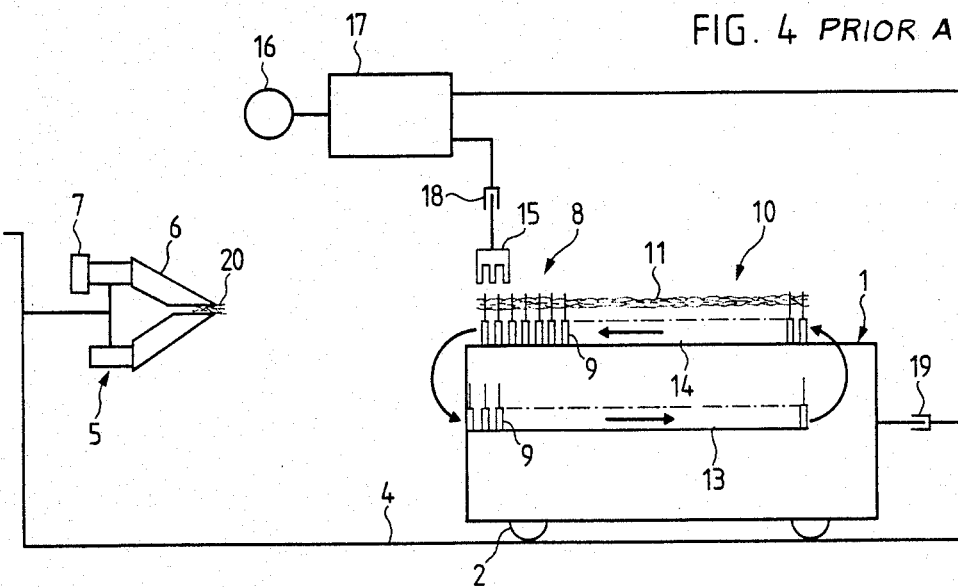
FIG. 4 shows the preparation of the prior art apparatus for the extraction of a succeeding fiber sample.

In FIG. 4, the pressing-in device 15 is raised and the furthest forward needle comb 9 has been conveyed into the lower side 13. The complete needle field 8 is now advanced by one needle comb spacing, so that once again fiber ends are in the extraction position. Clamping member 5 is simultaneously opened and the fiber sample removed therefrom and this can be followed by the next extraction operation.

One major disadvantage of this prior art fiber aligning and sample extracting apparatus is that due to the relatively complicated construction, the individual apparatus cannot be performed in a randomly fast manner. During the advance and return travel of truck 1 it is impossible to avoid air tubulence, which can lead to a disorientation of the fibers and therefore to a falsification of the measurements. The conveying of the first needle comb 9 into the lower side 13 and the displacement of needle field 8, as well as the return of the needle combs to needle field 8 are complicated operations, which cannot be performed at a random speed and which can also be linked with a certain fiber loss. In view of the complicated construction of the apparatus, there are also large masses with long lever bars to move, which impair precision and the space requirements and maintenance expenditures are correspondingly high.

Referring now to FIGS. 5 through 12 wherein the improved apparatus of the invention is described, the dot dash line in FIG. 5 diagrammatically illustrates a casing 3, which forms the fixed or stationary part of the apparatus. The movable part of the apparatus is a clamping means which may be a clamping member 35. Jaw 36 brings about the opening and closing of clamping member 35 under the force of a drive 37, which may appropriately be an eccentric, a pneumatic cylinder or a lifting magnet. Only clamping member 35, which may be in the form of a gripper, is movable, and it moves out of the waiting position shown in FIG. 5 into the sample grasping position and back again. The movement of clamping member 35 need not be a linear movement. The change from the waiting position into the sample grasping position can be achieved by a pivoting movement or by a lifting movement.

Within casing 30 there are provided a lower sliver conveying and advancing means such as conveyor 42 and an upper sliver conveying and advancing means such as conveyor 43 whose drives 44, 45 are mounted on the shaft of drive gears 51, 52. Conveyor members 53, 54 are guided by means of drive gears 51, 52 and deflecting wheels 55, 56. It is essential that the upper strand 57 of the lower conveyor 42 and the lower strand 58 of the upper conveyor 43 are juxtaposed and serve to guide and feed the fabric 41 introduced between deflecting wheels 55, 56. In the vicinity of clamping point K, where the projecting fiber ends 62 of fabric 41 are located and exposed, guidance wheels 59, 60 are provided for guiding the conveyor members 53, 54, thereby permitting the arrangement of driving wheels 51, 52 of conveyors 42, 43 in spaced manner with respect to clamping point K.

Above the two strands 57, 58 a comb plate 63 is located, which can be raised and lowered by means of a lifting device 64. Needle rows 65 at right angles to the movement of sliver 41 are inserted in comb plate 63 and conveyor members 53, 54 have corresponding openings so that the needles of rows 65 may penetrate through or only into the fabric of sliver 41. Thus, sliver 41 is held against displacement during the extraction of a fiber sample.

A control 70 makes it possible to synchronize the movement of conveyor drives 44, 45, lifting device 64 and clamping member drive 38 to accomplish the automatic extraction of fiber samples. Control 70 is connected to drives 44, 45 by control lines 71, 72; to lifting drive 64 by control line 73, and to drive 38 of clamping member 35 by control line 74. Indicator 75 indicates the presence of the fiber ends 62, and indicators 76 and 77 indicate the position of the lifting drive 64 and the position of clamping member 35 respectively.

The extraction of fiber sample from sliver 41 will be described with reference to FIGS. 6 through 8 using the same reference numerals as in FIG. 5.

FIG. 6 shows the advance of clamping member 35 to clamping point K. Lifting drive 64 has lowered comb plate 63 so that the needles of needle combs 65 penetrate the fabric of sliver 41 to retain the sliver 41 against displacement. If indicator 75 indicates the presence of fiber ends 62, the jaws 36 of clamping member 35 are closed.

Figure 7:
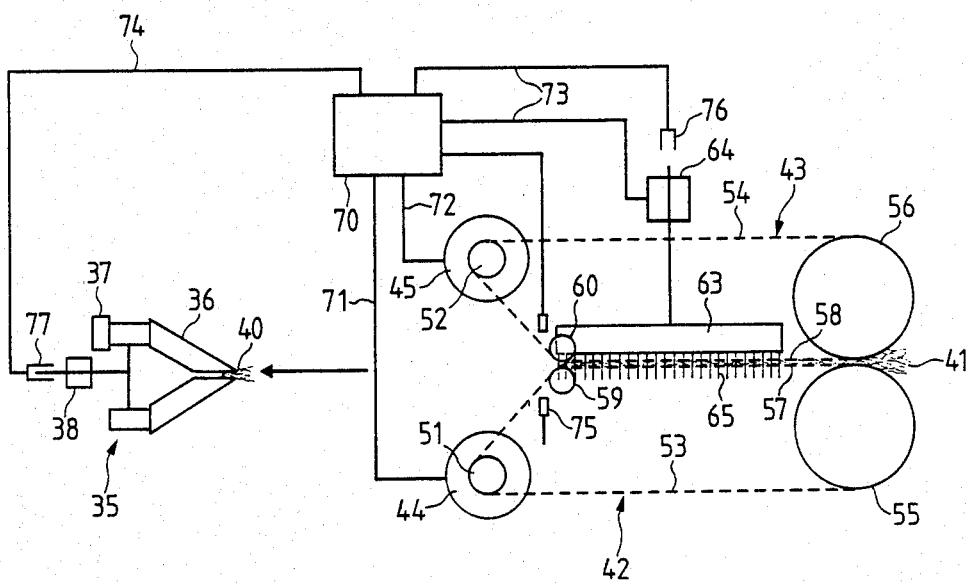
FIG. 7 shows the extraction of the fiber sample and the return of the clamping means of the invention to its waiting position.
Figure 8:
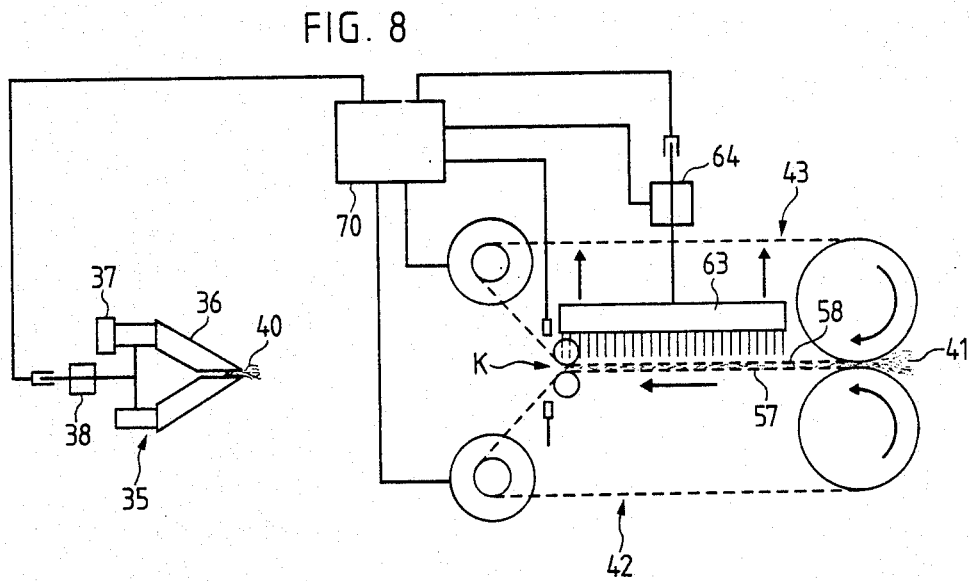
FIG. 8 shows the movement of the needles of the invention out of the sliver and the return of the apparatus to its waiting position just prior to the advance of the sliver.

In FIG. 7, clamping member 35 has extracted in end aligned manner a fiber sample 40 from sliver 41. FIG. 8 shows the completion of the extraction operation. Clamping member 35 is in position to open jaws 36 for removing the extracted fiber sample 40, comb plate has been raised by the lifting drive 64 so that the needless move out of the strands 57, 58 of conveyors 42,43 and out of sliver 41 so that conveyors 42, 43 can advance sliver 41 incrementally to project and expose new fiber ends at clamping point K.

Figure 9:
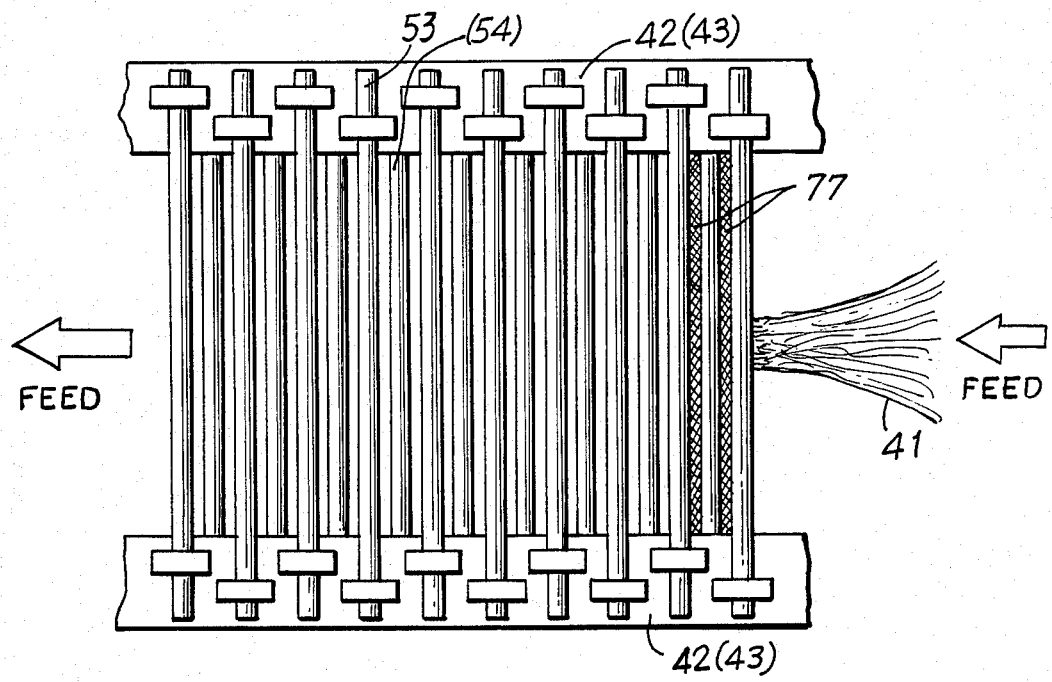
FIGS. 9 and 10 are respectively plan and vertical cross sectional detail views of the transverse rods and slots of the conveyors.
Figure 10:
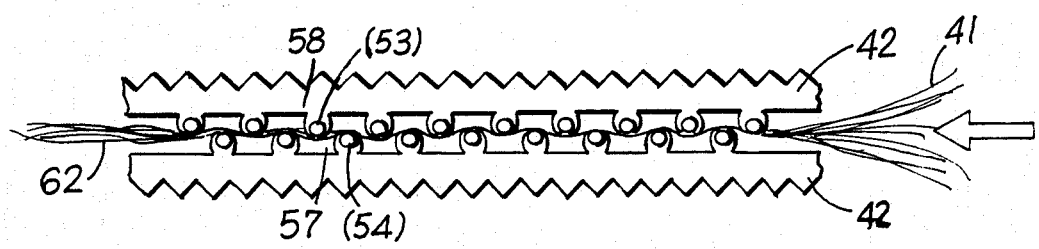

The conveyor members 53, 54 of conveyors 43, 42 can be constructed in various ways. It is important that they have transverse slots whose spacing 77 (as shown in FIG. 9) corresponds to that of the needle rows 65 of comb plate 63. For example, two spaced juxtaposed belts may be used, transverse rods being fixed at their ends in the belts. The internal width between the belts is somewhat larger than the width of the needle rows 65 of comb plate 63. Alternatively, each conveyor member may comprise two spaced link chains, in which the transverse rods form the joint spindles of the chain linkage. However, it is also possible to use a flat belt in which the slots corresponding to needle rows 65 are formed.

Lifting drive 64, as well as the drive 38 of clamping member 35 can be constructed as electromechanical hydraulic, pneumatic or electromagnetic drives. The movement of clamping member 35 to clamping point K can be a linear, pivoting or lifting movement. The drives 44,45 of conveyors 42, 43 may be stepping motors which make it possible to precisely maintain the desired incremental advance.

However, the drives of conveyors 42, 43 can also be driven in some other way, e.g. by pneumatic or electric pawl drives.

In place of the two conveyors 42, 43, it is also possible to use only the lower conveyor 42 for the advance of sliver 41. In this case, additional means may be used for sesuring the sliver to the envelope member 53 of the lower conveyor 42 such as by suction or electrostatic charge.

The advantages of the above-described fiber aligning and sample extraction apparatus are a mechanically simple solution, a simpler control technology, smaller dimensions, reduced air turbulence, precise functions, reduced susceptibility to dirtying, exact guidance of the fibers, smaller fiber loss and better maintenance possibilities. Particular advantage is also obtained from the better susceptibility to automation because the complete control is designed as a follow-up or sequence control, and the supply of sliver 41 can aslo be automated.

Figure 11:
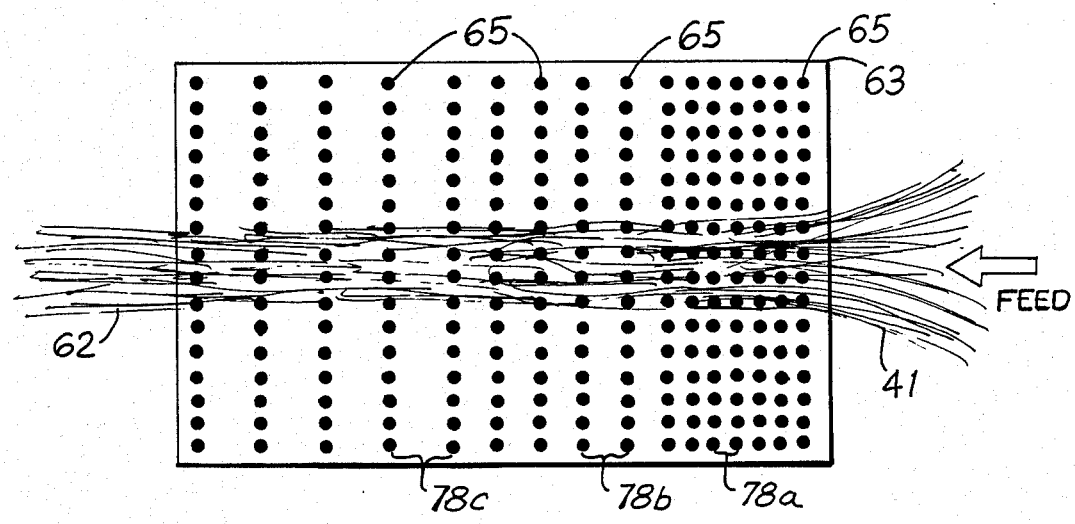
FIG. 11 is a plan detail view illustrating the arrangement of the needles in rows of variable spacing.

It will be appreciated that the spacing of the needles of needle combs 65 can be varied, because the combs do not change their position in comb plate 63. There is also no need to move individual needle combs 65, so that the spacing of the combs can be very small and correspondingly the clamping zone of the fiber end 62 can be smaller. As shown in FIG. 11, needle combs have variable needle distances 78a, 78b and 78c.

The method steps of the invention thus include, first, the successive incremental advancement of sliver 41 by such means as conveyors 42, 43 into its sample extraction position with the fiber end 62 exposed while the needles of needle comb 65 are raised out of the sliver and the clamping member 35 in its waiting position. Then the needles of needle comb 63 are driven into the sliver 41 and the clamping member 35 is moved into its end-grasping position and caused to grasp the fiber ends 62. The clamping member is then moved away from the sliver 41 to extract the sample and the needles are thereafter raised out of the sliver to permit the operation to be repeated.

While the method and apparatus have been described above in connection with one embodiment of the apparatus involved, it will be appreciated that modifications may be made and it it intended by the appended claims to cover all such modifications as fall within the broad scope of the inventions described.

I claim:

1. Apparatus for aligning and extracting fiber samples from the end of a sliver of material having top and bottom surfaces, comprising means for supporting and incrementally advancing the sliver into a sample extracting position with the sliver end exposed for extraction, the means for supporting and advancing the sliver including top and bottom conveyors which respectively engage the top and bottom surfaces of the sliver and at least the top conveyor contains openings for permitting the passage of needles into and out of the sliver; means for retaining the sliver against displacement while in its sample extraction position, the retaining means including said needles held in a needle comb plate and means for raising and lowering the needle comb plate to move the needles into and out of the sliver; clamping means for grasping the exposed sliver end while the sliver is retained in its sample extraction position; and means for moving the clamping means toward and away from the sliver end thereby to grasp and extract the fiber sample.

2. The apparatus of claim 1 wherein the openings comprise slots transverse to the direction of advancement of the sliver.

3. The apparatus of claim 1 wherein the conveyors comprise transverse rods which define transverse slots, said rods being supported and driven by linkages at the ends thereof.

4. The apparatus of claim 15 also comprising means for synchronizing the movement of the needle comb plate with the incremental advance of the sliver.

5. The apparatus of claim 1 wherein the needles are arranged in rows of variable spacing.

6. The apparatus of claim 1 also comprising means for synchronizing the retention of the sliver by the retaining means to follow each advancement of the sliver into its sample extracting position, and means for synchronizing the movement of the clamping means away from the sliver end to occur during each retention of the sliver in its sample extracting position.

* * * * *